United States Patent [19]

Van Der Puy et al.

[11] Patent Number: 4,537,614

[45] Date of Patent: Aug. 27, 1985

[54] S-ARYL AND S-ALIPHATIC DIAMIDOPHOSPHOROTHIOLATES AS UREASE INHIBITORS AND UREASE INHIBITED UREA BASED FERTILIZER COMPOSITIONS

[75] Inventors: Michael Van Der Puy, Cheektowaga, N.Y.; Jaroslav F. Kolc, Randolph Township, Dover County, N.J.; Louis G. Anello, Hamburg; Larry L. Hendrickson, Camillus, both of N.Y.; Milorad M. Rogic, Whippany; Michael D. Swerdloff, Parsippany, both of N.J.

[73] Assignee: Allied Corporation, Morris Township, Morris County, N.J.

[21] Appl. No.: 575,787

[22] Filed: Feb. 3, 1984

Related U.S. Application Data

[63] Continuation-in-part of Ser. No. 475,988, Mar. 16, 1983, abandoned.

[51] Int. Cl.³ .................................................. C05C 9/00
[52] U.S. Cl. .............................................. 71/28; 71/902
[58] Field of Search ............................... 71/11, 27–30, 71/902

[56] References Cited

PUBLICATIONS

1978, CA, vol. 89, Abst. #89:89455k, Matzel et al.
1979, CA, vol. 90, Abst. #90:21340j, Oertel et al.
1979, CA, vol. 91, Abst. #91:122724p, Matzel et al.
1979, CA, vol. 91, Abst. #91:139619f, Heber et al.
1981, CA, vol. 94, Abst. #94:101951g, Vlek et al.
1981, CA, vol. 94, Abst. #94:139429f, Bayless et al.

*Primary Examiner*—Ferris H. Lander
*Attorney, Agent, or Firm*—R. C. Stewart, II; J. P. Friedenson

[57] ABSTRACT

Novel urease inhibiting phosphorothiolate compounds, urea based fertilizer compositions including such compounds, and methods and compositions for using such compounds to inhibit the activity of urease.

31 Claims, No Drawings

S-ARYL AND S-ALIPHATIC DIAMIDOPHOSPHOROTHIOLATES AS UREASE INHIBITORS AND UREASE INHIBITED UREA BASED FERTILIZER COMPOSITIONS

RELATED APPLICATION

This application is a continuation-in-part application of application Ser. No. 475,988 filed Mar. 16, 1983, now abandoned.

BACKGROUND OF INVENTION

1. Field of the Invention

This invention relates to diamidophosphorothiolate urease inhibitors and urease inhibited urea based fertilizer compositions. More particularly, this invention relates to urease inhibited urea based fertilizer compositions which contain certain diamidophosphorothiolate compounds as the urease inhibitors, and to methods and compositions of inhibiting the catalytic activity of urease through application of such phosphorothiolate compounds to some plant growth media.

2. The Prior Art

It is well known in the art to use urea and urea compositions in fertilizers for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonia, when urea is placed under or on the surface of soil which contains urease. Urease, a crystallizable enzyme occurring in numerous bacteria and fungi, as for example *Micrococcus urease,* catalyzes the conversion of urea into ammonia and carbon dioxide. The reactions are as follows:

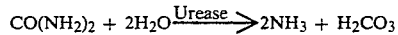

A portion of the ammonia thus formed is held by absorbing constituents of the soil and is available to plants as nutrient. However, a large amount of the ammonia may be lost to the air. A further problem resulting from the action of urease is that the accumulation of ammonium in the soil may cause damage to germinating seedlings and young plants.

One approach to reduction of problems resulting from the activity of soil urease toward soil applied urea is to find compounds that inhibit urease activity when applied to soils in conjunction with fertilizer urea. This approach has received considerable attention, and several classes of compounds have been used as urease inhibitors.

For example, some prior art describes various phosphoro compounds which are useful as urease inhibitors. Illustrative of such prior art are East German Pat. Nos. 142,714, 212,026, 122,177, 122,621 and 130,936 and Great Britain Pat. No. 1,494,774 which describe various phosphorodiamidate compounds as urease inhibitors. U.S. Pat. No. 4,242,325 describes a method of controlling the enzymatic decomposition of urea to ammonia and carbonic acid due to the action of urease, which method comprises exposing the enzyme to certain phosphoric triamide compounds. U.S. Pat. No. 4,182,881 describes the use of certain N-(diaminophosphinyl)arylcarboxyamide compounds as inhibitors of the enzyme urease in the urinary tract. U.S. Pat. No. 4,225,526 describes the use of 8-[(4-aminophenyl)-sulfonyl]amino-2-napthalenyl phosphorodiamidate compounds as inhibitors of the enzyme urease, and U.S. Pat. No. 4,222,948 describes the use of ([(4-aminophenyl)sulfonyl]amino)-phenyl phosphorodimidates as inhibitors of the enzyme urease.

Still other prior art describes the use of certain phosphoric triamide compounds for other purposes. For example, Great Britain Pat. No. 830,800 describes certain phosphoric triamide compounds which are useful as flame proofing agents.

SUMMARY OF THE INVENTION

In accordance with the present invention, there is provided a unique fertilizer composition comprising urea or a compound which is capable of forming urea when subjected to the use conditions of the composition and a "urease inhibiting effective amount" of one or more diamidophosphorothiolate compounds of the formula:

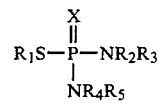

wherein
X is oxygen or sulfur;
$R_1$ is substituted or unsubstituted alkyl, cycloalkyl, heterocycle, alkenyl, alkynyl, aralkyl, aryl or alkaryl, wherein permissible substituents are one more trihalomethyl, acyloxy, isocyano, isocyanato, alkyl, halogen, alkylmercapto, arylmercapto, phenoxy, phenyl, nitro, quaternary ammonium radical, cyano, amino, hydroxy, alkylamino, dialkylamino, arylamino, diarylamino, alkoxy, aryloxy, mercapto, alkylmercapto, arylmercapto, alkylcarbonyl, arylcarbonyl, carboxy and carbonamide; and
$R_2$, $R_3$, $R_4$ and $R_5$ are the same or different and are hydrogen or alkyl having from 1 to about 4 carbon atoms. In the present specification and claims, the term "phosphorothiolate compounds" is used to refer to the above reference compounds.

Another aspect of this invention relates to a method of enhancing the yield and/or growth of plants which comprises applying the composition of this invention to the "plant growth media" in which the plants are being grown within reach of the root system of the plants (hereinafter referred to as "root zone"). As used herein, the term "plant growth media" refers to the various natural and artificial media which support plant growth, including but not limited to soil, potting mixtures of organic and inorganic matter, and artificial plant growth media such as polyurethane foam.

Yet another aspect of this invention relates to a method of inhibiting the urease catalyzed hydrolysis of urea at some situs, as for example a plant growth media which comprises applying a "urease inhibiting effective amount" of one or more of the above-mentioned phosphorothiolate compounds to the plant growth media or other situs prior to, after or in conjunction with the application of urea to said plant growth media or other situs. Still another aspect of this invention relates to a composition comprising a "urease inhibiting effective amount" of one or more of such phosphorothiolate compounds useful for carrying out such method. As used herein, a "urease inhibiting effective amount" is an amount of such phosphorothiolate compounds which when admixed with urea is capable of inhibiting the urease catalyzed hydrolysis of such urea to any extent.

It has been discovered that by applying a urease inhibiting effective amount of one or more of the aforementioned phosphorothiolate compounds in the said plant growth media or other situs, the urease catalyzed hydrolysis of the urea to ammonia is suppressed, thereby retarding the rate at which urea is lost from the media or situs. Furthermore, by proper distribution and/or application of the one or more phosphorothiolate compounds, this action of inhibiting the hydrolysis of urea to ammonia is effective over a prolonged period of time.

DETAILED DESCRIPTION OF THE INVENTION

The application of a urease inhibiting effective amount of one or more of the above-identified phosphorothiolate compounds to a plant growth media or other situs or inclusion thereof in a composition and application and/or distribution of the composition to a plant media or other situs is essential for the practice of this invention. While the phosphorothiolate compounds can be used to inhibit the urease hydrolysis of urea at any situs, they are especially useful for such inhibition in an agricultural context by application thereof, either alone or as a component of a composition, to a plant growth media. The amount of one or more phosphorothiolate compounds applied to or impregnated or distributed in the plant growth media is dependent on the amount of urea applied to the media. Preferably the amount of the phosphorothiolate compounds applied to, or impregnated or distributed in the plant growth media is an amount which is sufficient to inhibit the urease catalyzed hydrolysis of all or substantially all of the urea present in the composition containing the compound or in the plant growth media to which the compounds are being applied. Usually, in the practice of the invention, the amount of the phosphorothiolate compounds applied to, or impregnated or distributed in the plant growth media is at least about 0.01 parts of said one or more phosphorothiolate compounds per one million parts of said plant growth media. Hereinafter the abbreviation "p.p.m." is used to refer to parts of one or more phosphorothiolate compounds per million parts of plant growth media. In the preferred embodiments of this invention, the amount of said phosphorothiolate compounds distributed in said plant growth media is from about 0.01 to about 5,000 p.p.m., and in the particularly preferred embodiments is from about 0.2 to about 1000 p.p.m. on the same basis. Amongst these particularly preferred embodiments of the invention, most preferred are those embodiments of the invention in which the amount of said one or more phosphorothiolate compounds distributed in said plant growth media is from about 10 p.p.m. to about 500 p.p.m.

Within the above referenced limits, the particular amount of one or more phosphorothiolate compounds is dependent upon the particular situation. Thus, in determining the amount to be employed in any particular situation, consideration is made not only of the treatment need, i.e., soil pH, temperature, soil type, etc., but also of the mode of application to the plant growth media, the amount of urea being protected from urease catalyzed hydrolysis, etc. When the one or more phosphorothiolate compounds are to be applied in a broadcast application, the amount in p.p.m. may frequently be less than in row or band application where, for a substantial depth and width within the vicinity of application, there can be a very high concentration of the one or more phosphorothiolate compounds. When application is made near the root zone of growing plants, or when application is made immediately prior to seeding or transplanting, the amounts supplied are frequently at a lower rate than when application is made at the end of the growing season to prepare the soil for the following season. By dispersing very large dosages of the phosphorothiolate compounds in the plant growth media, a prolonged inhibition of the activity of urease can be obtained over a period of many months. The concentration of the one or more phosphorothiolate compounds is eventually reduced to a minimum by decomposition in the soil.

In one method for practicing the present invention, one or more phosphorothiolate compounds are distributed through all or a portion of the plant growth media in a broadcast application such as by spraying, dusting, distributing in irrigation water, and the like. In such application, the one or more phosphorothiolate compounds are supplied in amounts sufficient to permeate all or a portion the growing area of the plant growth media with a urease inhibiting effective amount of such phosphorothiolate compounds. In field administration, the one or more phosphorothiolate compounds can be applied to or near the surface of the plant growth media in an amount and through such cross-section of the media as to provide for the presence therein of a urease inhibiting effective amount of the one or more phosphorothiolate compounds. It is usually preferred that the one or more phosphorothiolate compounds be applied to the plant growth media in the immediate vicinity of the applied urea or at the situs where the urea will be applied, usually at or just below the surface of the plant growth media.

In another method for carrying out the present invention, one or more phosphorothiolate compounds are administered to a plant growth media in a band or row application. In such application, administration is made with or without carrier in amounts sufficient to supply to soil or plant growth media a urease inhibiting effective amount of the one or more phosphorothiolate compounds.

In one embodiment of the present invention, the one or more phosphorothiolate compounds are distributed throughout the growth media prior to seeding or transplanting the desired crop plant.

In another embodiment, the plant growth media in the root zone of growing plants is treated with the one or more phosphorothiolate compounds in an amount effective to inhibit the activity of urease but sublethal to plant growth. By following such practice, no adverse effect is exerted by the one or more phosphorothiolate compounds upon growth of seeds or plants. Oftentimes, it is desirable to treat the media adjacent to plants, and this procedure may be carried out conveniently in sidedressing operations.

In an additional embodiment, the plant growth media is treated with one or more phosphorothiolate compounds in conjunction with the application of urea or a compound capable of forming urea in situ on application to the plant growth media. Urea is a well known, commercially available compound and will not be discussed herein in detail. Illustrative of compounds which are believed to form urea on addition to the soil and are water soluble are urea and formaldehyde condensation products, as for example methylolureas, methyleneureas and mixtures thereof. These products and a method for their preparation are described in detail in U.S. Pat. No. 3,462,256. Still other useful sources of urea are water-insoluble urea formaldehyde condensation products such as ureaform. Illustrative of useful water-soluble urea and formaldehyde condensation products are those whose preparation and use are described in detail in U.S. Pat. Nos. 3,677,736 and 4,033,745.

The amount of urea or urea precursor compound included in the composition of this invention is not critical to the unique advantages thereof, and any amount known to those of skill in the art for use in fertilizers can be used. Normally, the amount employed will vary widely depending on a number of factors, including the times and frequency of application. In the preferred embodiments of the invention, the quantity of urea or urea precursor compound may vary from about 0.5 to about 99 weight percent based on the total weight of the composition. In those, particularly preferred embodiments in which the composition is applied in solid form, the amount of area present in the composition, may vary from about 30 to about 99 weight percent based on the total weight of the composition and in those particularly preferred embodiments in which the composition is applied in liquid form, the amount of urea may vary from about 1 to about 50 weight percent on the same basis. In the most preferred embodiments of this invention, the quantity of urea or urea precursor compound in liquid compositions will vary from about 3 to about 40 weight percent and in solid composition may vary from about 50 to about 99 weight percent on the aforementioned basis.

The fertilizer composition of this invention may include other optional ingredients known to those of skill in the art for inclusion in fertilizer compositions. For example, the composition may include sources of potassium, sulfur, phosphorus, boron, zinc, iron, manganese, copper, molybdenum, cobalt and like micronutrient and macronutrients which may be deficient in the soil. The composition may also include plant growth regulators, as for example auxins, cytokinins and the like, as well as pesticides, such as insecticides, miticides, herbicides, nematocides and the like; nitrification inhibitors and other urease inhibitors; and nonurea sources of nitrogen.

The present invention can be carried out by distributing the one or more phosphorothiolate compounds in an unmodified form through a plant growth media. The present method also embraces distributing one or more such compounds as a constituent in liquid or finely divided solid compositions. In such practice, the one or more phosphorothiolate compounds can be modified with one or more additaments or soil treating adjuvants including water, petroleum distillates or other liquid carriers, surface-active dispersing agents, inert finely divided solids and fertilizers such as urea or a compound capable of forming urea in situ. Preferred adjuvants are surface-active dispersing agents, inert finely divided solids, and especially, reduced nitrogen fertilizers; these adjuvants cooperate with the one or more phosphorothiolate compounds so as to facilitate the practice of the present invention and to obtain an improved result. Depending upon the concentration of the one or more phosphorothiolate compounds, augmented compositions can be distributed in the soil without further modification or can be considered as concentrates and subsequently diluted with additional inert carrier to produce the ultimate treating composition. The required amount of the phosphorothiolate can be supplied to growth media in from about 1 gallon (0.00378 m$^3$) to about 50 (0.189 m$^3$) gallons of organic solvent carrier, in from about 5 gallons (0.0189 m$^3$) to about 27,000 gallons (75.6 m$^3$) of aqueous carrier or in from about 20 to 2000 pounds of solid carrier per acre (22 to about 2200 kg/ha) treated. When an organic solvent carrier is employed, it can be further dispersed in the above volume of aqueous liquid carrier.

The concentration of the one or more phosphorothiolate compounds in compositions to be employed for the treatment of growth media is not critical, and can vary considerably provided the required dosage of effective agents is supplied to the growth media. In general, good results are obtained with liquid and/or solid compositions containing at least about 0.00001 weight percent of the phosphorothiolate compounds based on the total weight of the composition. Usually, however, the weight percent of the one of more phosphorothiolate compounds is from about 0.0001 to about 98 percent by weight of the one or more phosphorothiolate compounds on the same basis. In the preferred embodiments of the invention, the amount of the one or more phosphorothiolate compounds in the composition is from about 0.002 to about 50 weight percent, and in the particularly preferred embodiments is from about 0.01 to about 20 weight percent. Liquid or dust compositions in which the one or more phosphorothiolate compounds are present in higher concentration can be utilized as such or can be employed as concentrate compositions to be diluted to prepare actual treating compositions.

Liquid compositions containing the desired amount of the one or more phosphorothiolate compounds can be prepared by dispersing the latter in one or more liquid carriers such as water or an organic solvent with or without the aid of a suitable surface active dispersing agent or emulsifying agent. Suitable organic solvents include acetone, diisobutylketone, methanol, ethanol, isopropyl alcohol, diethyl ether, toluene, methylene chloride, chlorobenzene and petroleum distillates. The preferred organic solvents are those which are of such volatility that they leave little permanent residue in the growth media. Dispersing and emulsifying agents which can be employed in liquid compositions include condensation products of alkylene oxides with phenols and organic acids, alkylarylsulfonates, polyoxy-alkylene derivatives or sorbitol ester, sugar esters, complex ether alcohols, mahogany soaps and the like. The surface active agents are generally employed in the amount of from 1 to 20 percent by weight of the one or more phosphorotriolate compounds.

Solid compositions containing the active one or more phosphorothiolate compounds can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with one or more solid phosphorothiolate, wet with one or more liquid phosphorothiolate compounds or mixed with a solution or a dispersion of the one or more solid or liquid phosphorothiolate compounds in a volatile organic solvent. Depending upon the proportions of ingredients, these compositions can be employed without further modification or be considered concentrates and subsequently further diluted with solid surface active dispersing agents, talc, chalk, gypsum or the like to obtain the desired treating composition. Furthermore, such concentrate compositions can be dispersed in water with or without added dispersing agent or agents to prepare aqueous soil treating compositions.

Soil treating compositions can be prepared by dispersing one or more of the phosphorothiolate compounds in a urea fertilizer. The concentration of the one or more phosphorothiolate compounds employed in such compositions should, in general, be sufficient to inhibit the hydrolysis of all or a part of the urea in the fertilizer to ammonia when the fertilizer is distributed in a plant growth media. The resulting fertilizer composition can be employed as such or can be modified as by dilution with additional nitrogen fertilizer or with inert solid carrier to obtain a composition containing the desired amount of active agent for treatment of soil. Further, an aqueous dispersion of the one or more phosphorothiolate compounds and urea fertilizer composition can be prepared and administered to the growth media.

The composition of this invention can be conveniently prepared according to conventional methods known to those of skill in the art, and therefore such methods will not be described herein in great detail. Briefly stated, the various essential and optional ingredients can be granulated and mixed usually with a carrier and/or diluent, either liquid or solid. Suitable liquid carriers or diluents include water, petroleum distillates or other liquid carriers. Suitable solid carriers or diluents include clay, talc, bentonite, diatomaceous earth, fullers earth and the like.

While the composition and method of this invention are particularly suited for agricultural applications for prevention or inhibition of urease catalyzed hydrolysis of urea, they can also be used in other applications where inhibition of the activity of urease is desired. For example, such other applications include use in animal litters, as feed additives, diaper treatment, pharmaceutical applications, urease inhibition in mammalian urinary tracts and the like. It should be noted that the particular active compound employed in one application may not necessasrily be useful in another application. Thus, in the selection of a particular active material for use in an application, such factors as toxicity of the material, the environment in which the material will be used, level of urease inhibition desired and the like must be considered in selecting such material.

The novel phosphorothiolate compounds of this invention which are useful as urease inhibitors in the composition of this invention are those of the formula:

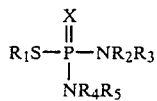

wherein:
X is oxygen or sulfur;
$R_1$ is substituted or unsubstituted alkyl, cycloalkyl, alkenyl, heterocycle, alkynyl, cycloalkyl, aralkyl, aryl or alkaryl, wherein permissible substituents are one or more trihalomethyl, acyloxy, alkyl, heterocycle, aryloxy, halogen, arylmercapto, phenoxy, phenyl, hydroxy, nitro, cyano, amino, alkylamino, dialkylamino, alkoxy, mercapto, alkylmercapto, arylmercapto, alkylcarbonyl, alkylcarbonyl, carboxy, arylamino, carbonamide and diarylamino; and
$R_2$, $R_3$, $R_4$ and $R_5$ are the same or different, and are individually hydrogen or to alkyl having from 1 to about 4 carbon atoms.

Illustrative of permissible $R_1$ substituents are 2-chloroethyl, 3-chloropropyl, 4-chlorobutyl, 2,2-dichloroethyl, pentyl, 2-cyanoethyl, iodomethyl, 2-phenoxyethyl, 3-bromopentyl, 5-chloropentyl, 2-methoxyneopentyl, tert-butyl, 2-iodo-2-phenylethyl, 4-isopropoxyethyl, 2,2,2-trichloroethyl, 2-naphthoxyethyl, 2,2-dichloropropyl, isopropyl, 3-mercaptobutyl, 2-acetylpropyl, 2,2,2-trifluoroethyl, 2,2,3,3-tetrachloropropyl, 4-phenoxybutyl, 2,2-dibromopropyl, 2-dimethylaminoethyl, 2-nitroethyl, 3-mercaptobutyl, 2-(p-toleunesulfonyl)propyl, ethyl, methyl, neopentyl, propyl, 2-butene, nonyl, ethylene, allyl, acetylene, cyclopropyl, cyclohexyl, 1-cyanoethyl, 1-chloro-prop-2-enyl, 2-cyano-but-3-enyl, 3-methoxypent-4-enyl, 1-iodo-2,2-dimethylprop-2-enyl, 3-methylaminobutyl, 4-chlorophenyl, 3-pyridyl, 2-furyl, 2-naphthyl, phenyl, benzyl, 3-nitrophenyl, 4-nitrophenyl, 4-halophenyl, 4-aminophenyl, 4-alkylphenyl, 4-alkoxyphenyl, 2-methylphenyl, 2,3-dimethylphenyl, 3-trifluoromethylphenyl, 4-cyanophenyl, 3-phenoxyphenyl, biphenyl, 2,4-dichlorophenyl, 2,4,6-trimethylphenyl, 3-pyridyl, cinnamenyl and the like.

Examples of useful $R_2$, $R_3$, $R_4$ and $R_5$ substituents are hydrogen, methyl, ethyl and propyl.

The following compounds are illustrative of phosphorothiolate compounds within the scope of the generic formula set forth above which can be prepared in accordance with the procedures set forth hereinbelow and which can be employed in the practice of this invention.

S-Propyl Diamidophosphorothiolate
S-Cyclohexyl Diamidophosphorothiolate
S-(2-Furyl) Diamidophosphorothiolate
S-(2-Imidazolyl) Diamidophosphorothiolate
S-(2-Benzimidazolyl) Diamidophosphorothiolate
S-(3-Amino-5-(1,2,4-triazolyl)) Diamidophosporothiolate
S-(5-Amino-2-(1,3,4-thiadiazolyl)) Diamidophosphorothiolate
S-(2-Thiazolinyl) Diamidophosphorothiolate
S-(2-Benzothiazolinyl) Diamidophosphorothiolate
S-(2-Benzooxazolyl) Diamidophosphorothiolate
S-(5-Hydroxy-3-pyrazolyl) Diamidophosphorothiolate
S-(2-Quinazolinonyl) Diamidophosphorothiolate
S-(1,2,2-Trichlorovinyl) Diamidophosphorothiolate
S-Benzyl Diamidophosphorothiolate
S-(1-Naphthyl) Diamidophosphorothiolate
S-(4-Acetamidophenyl) Diamidophosphorothiolate
S-(4-Methylphenyl) Diamidophosphorothiolate
S-(3-Chlorophenyl) Diamidophosphorothiolate
S-(2-Phenoxyethyl) Diamidophosphorothiolate
S-Allyl Diamidophosphorothiolate
S-2-(Ethylthio)ethyl Diamidophosphorothiolate
S-Methyl Diamidophosphorothiolate
S-(Ethoxycarbonylmethyl) Diamidophosphorothiolate
N-Methyl-S-butyl Diamidophosphorothiolate
S-Hexyl Diamidophosphorothiolate
S-(2,4-Dimethylphenyl) Diamidophosphorothiolate
S-(2-Propargyl) Diamidophosphorothiolate
S-(4-Allylphenyl) Diamidophosphorothiolate
S-(Trichloromethyl) Diamidophosphorothiolate S-(2-Methyl-4-hydroxyphenyl) Diamidophosphorothiolate
S-(2-Methoxyphenyl) Diamidophosphorothiolate
S-(4-Propoxyphenyl) Diamidophosphorothiolate
S-(2-Mercaptophenyl) Diamidophosphorothiolate
S-(2-Chloro-3-hydroxycyclohexyl) Diamidophosphorothiolate
S-(4-Trifluoromethylphenyl) Diamidophosphorothiolate
S-(4-Trichloromethylphenyl) Diamidophosphorothiolate
S-(2,4-Dinitrophenyl) Diamidophosphorothiolate
S-(2-Phenoxyethyl) Diamidophosphorothiolate
S-(3-Hydroxyphenyl) Diamidophosphorothiolate
S-Heptyl Diamidophosphorothiolate
S-Pentyl Diamidophosphorothiolate
S-Octyl Diamidophosphorothiolate
S-Phenyl Diamidophosphorothiolate
S-Naphthyl Diamidophosphorothiolate
S-(3-Pyridyl) Diamidophosphorothiolate
S-(2-Thienyl) Diamidophosphorothiolate
S-(2-Pyrimidinyl) Diamidophosphorothiolate
S-(2-Pyrazinyl) Diamidophosphorothiolate
S-(2-Piperidinyl) Diamidophosphorothiolate
S-(2-Pyrrolidinyl) Diamidophosphorothiolate
S-(Morpholinyl) Diamidophosphorothiolate
S-(2-Propenyl) Diamidophosphorothiolate
S-(3-Hexenyl) Diamidophosphorothiolate
S-(3-Phenylhexyl) Diamidophosphorothiolate
S-(3-Phenyloctyl) Diamidophosphorothiolate
S-(3-Methoxypent-4-enyl) Diamidophosphorothiolate
S-(1-Iodo-2-methylprop-2-enyl) Diamidophosphorothiolate
S-(3-Cyanocyclopentyl) Diamidophosphorothiolate
S-Propynyl Diamidophosphorothiolate
S-(4-Phenylmercaptophenyl) Diamidophosphorothiolate
S-(2-Acetylpropyl) Diamidophosphorothiolate
S-(2-Hydroxyethyl) Diamidophosphorothiolate
S-(2-Phenylethyl) Diamidophosphorothiolate
S-(3-Naphthylpropyl) Diamidophosphorothiolate
S-(Cyclopropyl) Diamidophosphorothiolate
S-(Cyclohexyl) Diamidophosphorothiolate
S-Cyclopentyl) Diamidophosphorothiolate
S-(2-Chlorocyclohexyl) Diamidophosphorothiolate
S-(3-Methylthioethyl) Diamidophosphorothiolate
S-(3-Chlorophenylethyl) Diamidophosphorothiolate
S-(3-Thiocyanopentyl) Diamidophosphorothiolate
S-(2,4-Dimethylphenylpropyl) Diamidophosphorothiolate
S-Propyl Diamidothiophosphorothiolate
S-Cyclohexyl Diamidothiophosphorothiolate
S-(2-Furyl) Diamidothiophosphorothiolate
S-(2-Imidazolyl) Diamidothiophosphorothiolate
S-(2-Benzimidazolyl) Diamidothiophosphorothiolate
S-(3-Amino-5-(1,2,4-triazolyl)) Diamidothiophosphorothiolate
S-(5-Amino-2-(1,3,4-thiadiazolyl)) Diamidothiophosphorothiolate
S-(2-Thiazolinyl) Diamidothiophosphorothiolate
S-(2-Benzothiazolinyl) Diamidothiophosphorothiolate
S-(2-Benzooxazolyl) Diamidothiophosphorothiolate
S-(5-Hydroxy-3-pyrazolyl) Diamidothiophosphorothiolate
S-(2-Quinazolinonyl) Diamidothiophosphorothiolate
S-(1,2,2-Trichlorovinyl) Diamidothiophosphorothiolate
S-Benzyl Diamidothiophosphorothiolate
S-(1-Naphthyl) Diamidothiophosphorothiolate
S-(4-Acetamidophenyl) Diamidothiophosphorothiolate
S-(4-Methylphenyl) Diamidothiophosphorothiolate
S-(3-Chlorophenyl) Diamidothiophosphorothiolate
S-(2-Phenoxyethyl) Diamidothiophosphorothiolate
S-Allyl Diamidothiophosphorothiolate
S-2-(Ethylthio)ethyl Diamidothiophosphorothiolate
S-Methyl Diamidothiophosphorothiolate
S-(Ethoxycarbonylmethyl) Diamidothiophosphorothiolate
N-Methyl-S-butyl Diamidothiophosphorothiolate
S-Hexyl Diamidothiophosphorothiolate
S-(2,4-Dimethylphenyl) Diamidothiophosphorothiolate
S-(2-Propargyl) Diamidothiophosphorothiolate
S-(4-Allylphenyl) Diamidothiophosphorothiolate
S-(Trichloromethyl) Diamidothiophosphorothiolate
S-(2-Methyl-4-hydroxyphenyl) Diamidothiophosphorothiolate
S-(2-Methoxyphenyl) Diamidothiophosphorothiolate
S-(4-Propoxyphenyl) Diamidothiophosphorothiolate
S-(2-Mercaptophenyl) Diamidothiophosphorothiolate
S-(2-Chloro-3-hydroxycyclohexyl) Diamidothiophosphorothiolate
S-(4-Trifluoromethylphenyl) Diamidothiophosphorothiolate
S-(4-Trichloromethylphenyl) Diamidothiophosphorothiolate
S-(2,4-Dinitrophenyl) Diamidothiophosphorothiolate
S-(2-Phenoxyethyl) Diamidothiophosphorothiolate
S-(3-Hydroxyphenyl) Diamidothiophosphorothiolate
S-Heptyl Diamidothiophosphorothiolate
S-Pentyl Diamidothiophosphorothiolate
S-Octyl Diamidothiophosphorothiolate
S-Phenyl Diamidothiophosphorothiolate
S-Naphthyl Diamidothiophosphorothiolate
S-(3-Pyridyl) Diamidothiophosphorothiolate
S-(2-Thienyl) Diamidothiophosphorothiolate
S-(2-Pyrimidinyl) Diamidothiophosphorothiolate
S-(2-Pyrazinyl) Diamidothiophosphorothiolate
S-(2-Piperidinyl) Diamidothiophosphorothiolate
S-(2-Pyrrolidinyl) Diamidothiophosphorothiolate
S-(Morpholinyl) Diamidothiophosphorothiolate
S-(2-Propenyl) Diamidothiophosphorothiolate
S-(3-Hexenyl) Diamidothiophosphorothiolate
S-(3-Phenylhexyl) Diamidothiophosphorothiolate
S-(3-Phenyloctyl) Diamidothiophosphorothiolate
S-(3-Methoxypent-4-enyl) Diamidothiophosphorothiolate
S-(1-Iodo-2-methylprop-2-enyl Diamidothiophosphorothiolate
S-(3-Cyanocyclopentyl) Diamidothiophosphorothiolate
S-Propynyl Diamidothiophosphorothiolate
S-(4-Phenylmercaptophenyl) Diamidothiophosphorothiolate
S-(2-Acetylpropyl) Diamidothiophosphorothiolate
S-(2-Hydroxyethyl) Diamidothiophosphorothiolate
S-(2-Phenylethyl) Diamidothiophosphorothiolate
S-(3-Naphthylpropyl) Diamidothiophosphorothiolate
S-(Cyclopropyl) Diamidothiophosphorothiolate
S-(Cyclohexyl) Diamidothiophosphorothiolate
S-(Cyclopentyl) Diamidothiophosphorothiolate
S-(2-Chlorocyclohexyl) Diamidothiophosphorothiolate
S-(3-Methylthioethyl) Diamidothiophosphorothiolate
S-(3-Chlorophenylethyl) Diamidothiophosphorothiolate
S-(3-Thiocyanopentyl) Diamidothiophosphorothiolate S-(2,4-Dimethylphenylpropyl) Diamidothiophosphorothiolate Preferred for use in the practice of this invention are phosphorothiolate compounds in which:

X is oxygen or sulfur; and $R_1$ is alkyl, or substituted alkyl having one or more substituents at the alpha, beta and/or gamma carbon atoms relative to the sulfur atom to which said $R_1$ group is substituted, wherein permissible substituents are selected from the group consisting of iodo, chloro, phenyl, bromo, fluoro, phenoxy, p-nitrophenoxy, phenyl, or phenyl substituted with 3-nitro, 4-nitro, 4-halo, 4-amino, 4-alkyl, 4-cyano, 4-alkoxy, 3-phenoxy, 3-pyridyl, 2-furyl, 2-naphthyl and cinnamenyl; and $R_2$, $R_3$, $R_4$ and $R_5$ are individually hydrogen or methyl.

Particularly preferred for use in this invention are compounds in which:

X is oxygen or sulfur;

$R_1$ is alkyl having from 1 to about 8 carbon atoms; and $R_2$, $R_3$, $R_4$ and $R_5$ are hydrogen.

Especially efficacious compound for use in the practice of this invention are S-methyl diamidophosphorothiolate, S-(n-butyl) diamidophosphorothiolate, S-(2-butyl) diamidophosphorothiolate, S-(iso-butyl) diamidophosphorothiolate, S-(n-hexyl) diamidophosphorothiolate and S-(cyclohexyl) diamidophosphorothiolate. Amongst the above listed compounds, S-(n-butyl) diamidophosphorothiolate, S-(iso-butyl) diamidophosphorothiolate, and S-(n-hexyl) diamidophosphorothiolate were most efficacious, primarily because of relatively long term residual activity.

Compounds for use in the practice of this invention can be prepared in accordance with the following Reaction Scheme A:

Reaction Scheme A

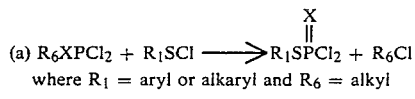

where $R_1$ = aryl or alkaryl and $R_6$ = alkyl

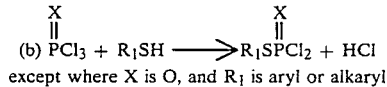

except where X is O, and $R_1$ is aryl or alkaryl

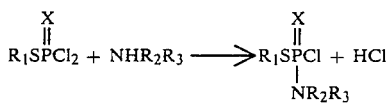

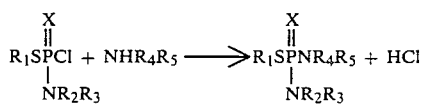

The aforementioned reaction is a modification of the procedure described in more detail in East German Patent No. 128,315; Roth, H. J., et al., SYNTHESIS OF PHENYL PHOSPHORODIAMIDATES. PART I., Arch. Pharm., 314 85–91, and references cited therein; E. Cherbuliez, in "Organic Phosphorus Compunds" ed. G. M. Kosolapoff and L. Maier vol. 6, Chapter 15, Wiley Interscience, 1973; and E. Fluck and W. Carubala ibid., Chapter 16, and L. N. Shitov and M. Gladshtein, J. Gen. Chem. USSR 1968, 38, 2268. Accordingly the reaction will not be described herein in any great detail.

Briefly stated, in each step of the three step reaction sequence, substantially equal molar amounts or excesses of the reactants are contacted neat or preferably in an inert solvent optionally in the presence of a hydrogen chloride acceptor. The order in which the various reactants are reacted as indicated in the above reaction sequence is only for illustrative purposes, and the order of reaction is not critical. Inert solvents which can be used in this reaction include benzene, ethyl ether, toluene, tetrahydrofuran, carbon tetrachloride, xylene, dioxane, methylene chloride, dimethylformamide, methyl sulfoxide and the like.

Useful acid acceptors are non-nucleophilic compounds which can react with the proton by-product to form a chloride salt and can be either an inorganic or organic base. Suitable acid acceptors include alkali metal carbonates such as sodium and potassium carbonates. Useful and preferred organic bases for use in the practice of this invention are tertiary amines such as pyridine, triethylamine, trimethylamine, isoquinoline, quinoline, lutidine, tributylamine, N-ethylpiperidine, 1,4-diazabicyclo[2,2,2]octane and the like. Alternatively, an excess of the amine reactant can be used as the acid acceptor.

Reaction temperatures are not critical and can be varied widely. For example, the reaction can be conveniently carried out in a temperature of from about $-30°$ C. to about 200° C., but is preferably carried out at a temperature of from about $-20°$ C. to about 125° C.

Similarly, reaction pressures are not critical and can be varied widely. For example, the reaction can be carried out at sub-atmospheric, atmospheric or superatmospheric pressure. However, for convenience, the reaction is carried out at atmospheric or autogeneous pressure.

The exact proportions of the reactants are not critical, some of the desired product being obtained when the reactants are employed in any proportions. However, in going to completion, the reaction consumes the reactants and the hydrogen chloride acceptor in equimolar proportions, and the use of the reactants and the hydrogen chloride acceptor in such proportions is preferred.

Reaction times are also not critical and can be varied widely. The mixture is usually held within the desired reaction temperature range for a period of time conveniently from about 2 to 8 hours before cooling. Good yields are obtained with reaction times of about 4 to 5 hours.

During the reaction, the hydrochloride salt of the hydrogen chloride acceptor forms and may precipitate from the mixture. This salt can be removed by such conventional procedures as extraction, filtration or centrifugation. The desired phosphorothiolate compound can be separated by such conventional procedures as evaporation and purified by conventional procedures such as distillation and extraction. The product separated as described above may be employed in the control of urease in soil or in other applications where urease inhibition is desired or may be further purified by conventional procedures such as extraction and distillation.

The following specific examples are presented to more particularly illustrate the invention.

EXAMPLE I

The Preparation of S-Methyl Phosphorodichloridothiolate

Into a 200 mL, 3-necked flask fitted with a stirrer, reflux condenser and thermometer was charged 50 mL of anhydrous diethyl ether. The flask was cooled to −25° C. and 25 g (0.52 mole) of methyl mercaptan was added to the flask through a gas inlet tube. After the addition of the mercaptan was complete, 80 g (0.52 mole) of phosphorus oxychloride was slowly dropped into the cooled mixture. Reflux at 5° C. to 10° C. produced no reaction and the mixture was cooled to −20° C. while 53 g (0.52 mole) of triethylamine was slowly added. After the exotherm subsided, the mixture was stirred at 5°–10° C. for 1 hour, and then allowed to warm to room temperature. An additional 30 mL of ether was added, and the mixture was filtered to remove solids and the filtrate was distilled. After removal of the ether, there was recovered 34 g (0.206 mole) (39.5% yield) of the desired S-methyl phosphorodichoridothiolate, bp 70°–74° C./10 mm of Hg, 10 g (0.057 mole) (22.7% yield) of a fraction having a bp 135°–142° C./10 mm and 20 g of still pot residue.

NMR(CDCl$_3$): δ 2.68 ppm (d, J=22–23 Hz).
IR (neat): 1265 cm$^{-1}$.

EXAMPLE II

The Preparation of S-Methyl Diamidophosphorothiolate

Into a 100 ml 3-necked flask fitted with stirrer, thermometer, condenser and a gas inlet tube was charged 3.5 g (0.021 mole) of S-methyl phosphorodichloridothiolate as prepared in Example I and 50 mL of anhydrous chloroform. The mixture was cooled to −25° C., afterwhich 15 g (0.88 mole) of anhydrous ammonia was added. The mixture was then stirred for 2 hours at −25° C., and then warmed to room temperature to remove excess ammonia. There was formed about 5 g of solids, which were filtered and then further extracted with hot methylene chloride in a Soxhlet extractor to give about 2.5 g (0.20 mole) of the desired S-methyl diamidophosphorothiolate mp 114°–118° C.

NMR (DMSO-d$_6$) δ 4.3 (bs, 4H) and 2.12 ppm (d, 3H, J=15 Hz).

EXAMPLE III

The Preparation of S-(n-Butyl) Diamidophosphorothiolate

A. Preparation of S-(n-Butyl) Phosphorodichloridothiolate

A solution of 25.5 mL (0.238 mole) of 1-butane thiol and 19.2 ml (0.238 mole) of pyridine in 200 mL of anhydrous ether was added dropwise to a stirred solution of 67 mL (0.714 mole) of phosphorus oxychloride in 200 mL of ether at room temperature. After the addition was complete, the mixture was refluxed for 1 h. The volatiles were stripped off in vacuo and the residue was extracted with 200 mL of pentane. After filtering, the filtrate was concentrated at reduced pressure to provide a yellow oil. The oil was distilled to yield 19.2 g (39%) of the desired S-(n-butyl) phosphorodichloridothiolate (bp=87°–92° C./0.3 mm of Hg).

NMR (CDCl$_3$): δ 3.20 (dt, 2, J=6, 21 Hz), 2.2–1.2 (cp, 4), and 0.98 ppm (t,3, J=6 Hz).

B. Preparation of S-(n-butyl) Diamidophosphorothiolate

S-(n-Butyl) phosphorodichloridothiolate was added as a solution in methylene chloride (80 mL) to a solution of 24 mL of anhydrous ammonia in 125 mL of methylene chloride. After the addition was complete and the mixture had warmed to room temperature, the inorganic salts were filtered and were continuously extracted with chloroform (2×500 mL) for 85 h. The combined organic phases were concentrated at reduced pressure to provide 7.5 g (48%) of S-(n-butyl) diamidophosphorothiolate as a white solid (mp=130°–134° C.).

NMR (DMSO-d$_6$): δ 4.38 (bs, 4), 2.65 (dt, 2, J=6, 21, Hz), 1.00–1.80 (cp, 4), and 0.80 ppm (t, 3, J=6 Hz).
IR (Nujol): 2.9–3.3 (b); and 8.5μ.
HPLC analysis indicated a purity of 93%.

EXAMPLE IV

The Preparation of S-(2-Butyl) Diamidophosphorothiolate

A. Preparation of S-(n-Butyl) Phosphorodichloridothiolate

A solution of sec-butyl thiol (26.3 mL, 0.242 mole) and 19.5 mL (0.242 mole) of pyridine in 100 mL of anhydrous ether was added dropwise to a stirred solution of 67.5 mL (0.724 mole) of phosphorus oxychloride in 200 mL of anhydrous ether at room temperature. The resultant slurry was stirred for 16 h, filtered and the filtrate concentrated at reduced pressure to provide an oil. The oil was distilled (bp=90°–105° C./1.2 mm of Hg) to yield 12.8 g (25.6%) of the desired S-(n-butyl) phosphorodichloridothiolate.

NMR (CDCl$_3$): δ 3.70 (cp, 1), 1.80 (cp, 2), 1.60 (d, 3, J=9 Hz), and 1.10 ppm (t, 3, J=9 Hz).
IR (neat film): 3.30, and 17.9μ.

B. Preparation of S-(n-Butyl) diamidophosphorothiolate

S-(2-Butyl) phosphorodichloridothiolate (0.062 mole) in 75 mL of methylene chloride was added dropwise to a stirred solution of 16 mL of anhydrous ammonia in 100 mL of methylene chloride. After the addition was complete and the mixture had warmed to room temperature, the inorganic salts were filtered and the filtrate was concentrated at reduced pressure to provide 4.0 g of a white solid. An additional 4.9 g was obtained by extracting the salts with chloroform (500 mL, reflux) for 24 h. The combined product (86%) was identified as S-(2-butyl) diamidophosphorothiolate (mp=85°–88° C.).

NMR (DMSO-d$_6$): δ 4.32 (bs, 4), 3.10 (cp, 1), 1.10–2.00 (cp, 5), and 1.00 ppm (t, 3).
IR (Nujol): 2.9–3.3 (b, s), and 8.4μ.
HPLC analysis indicated a purity of 88%.

EXAMPLE V

The Preparation of S-(iso-Butyl) Diamidophosphorothiolate

A. Preparation of S-(iso-Butyl) Phosphorodichloridothiolate

A solution of isobutyl mercaptan (25.9 mL, 0.238 mole) and pyridine (19.2 mL, 0.238 mole) in 100 mL of anhydrous ether was added dropwise to a stirred solution of 67 mL (0.714 mole) of phosphorus oxychloride in 200 mL of ether at room temperature. After addition and a subsequent 1 h reflux period were complete, the volatiles were vacuum stripped (35° C./5 mm of Hg) and the residue was extracted with 200 mL of pentane. After filtering and concentration of the filtrate, a yellow oil was isolated. The oil was distilled (100° C./2–3 mm of Hg) to yield 20.6 g (41.9%) of the desired S-(iso-butyl) phosphorodichloridothiolate.

NMR(CDCl$_3$): δ 3.10 (dd, 2, J=19.5, and 7.5 Hz), 2.10 (m, 1), and 1.11 ppm (d, 3, J=7.5 Hz);
IR (neat film): 3.38, 3.41, 3.45, 3.49 and 7.89μ

B. Preparation of S-(iso-Butyl) Diamidophosphorothiolate

S-(iso-Butyl) phosphorodichloridothiolate was added dropwise (in 90 mL of methylene chloride) to a solution of 25 mL of anhydrous ammonia in 130 mL of methylene chloride. After the addition was complete, the resultant slurry was slowly warmed to room temperature over a 16 h period. After filtering, the inorganic salts were continuously extracted with 2×500 mL of chloroform (at reflux) for 48 h to provide 11.4 g (61%) of the desired S-(iso-butyl) diamidophosphorothiolate as a white solid (mp=115°–118° C.).

NMR(DMSO-d$_6$): δ 4.40 (br, s, 4), 3.60 (dd, 2, J=10.5, 7.5 Hz), 1.82 (m, 1), and 0.90 ppm (d, 3, J=7.5 Hz).
IR(Nujol) 2.90, 2.95–3.20, and 8.60μ.
HPLC analysis indicated a purity of 86%.

EXAMPLE VI

The Preparation of S-(n-Hexyl) Diamidophosphorothiolate

A. Preparation of S-(n-Hexyl) Phosphorodichloridothiolate

Using the procedure of Example IV, 45 mL (0.319 mole) of 1 hexane thiol, 25.8 mL (0.319 mole) of pyridine in 132 mL of ether and 90 mL (0.957 mole) of phosphorus oxychloride were reacted in 264 mL of ether followed by distillation (bp=97°–108° C./0.25 mm of Hg), to provide 22 g (29%) of the desired S-(n-hexyl) phosphorodichloridothiolate.

NMR(CDCl$_3$): δ 3.20 (dt, 2) and 0.60–2.20 ppm (cp, 11);
IR (neat film): 3.4, and 7.89μ.

B. Preparation of S-(n-Hexyl) Diamidodichloridothiolate

Using the procedure of Example IV, S-(n-hexyl) phosphorodichloridothiolate was reacted with 24 mL of anhydrous ammonia in 200 mL of methylene chloride to provide 4.4 g (24%) of the desired S-(n-hexyl) diamidophosphorothiolate as a white solid (mp=116°–119° C.).

NMR (DMSO-d$_6$): δ 4.33 (s, 4), 2.60 (dt, 21, and 0.40–1.90 ppm (cp, 11).
IR(Nujol): 2.9–3.2 (b), and 8.60μ.
HPLC analysis indicated a purity of 94%.

EXAMPLE VII

The Preparation of S-(Cyclohexyl) Diamidophosphorothiolate

A. Preparation of S-(Cyclohexyl) Phosphorodichloridothiolate

Using the procedure of Example IV, 39.4 mL (0.321 mole) of cyclohexyl mercaptan, 26 mL (0.321 mole) of pyridine in 133 mL of ether, 90 mL (0.965 mole) of phosphorus oxychloride were reacted in 264 mL of ether followed by distillation (bp=115°–125° C./0.1 mm of Hg) to provide 13.4 g (18%) of the desired S-(cyclohexyl) phosphorodichloridothiolate.

NMR(CDCl$_3$): δ 3.70 (m, 1), and 0.70–2.60 ppm (cp, 10).

B. Preparation of S-(Cyclohexyl) Diamidophosphorothiolate

S-(Cyclohexyl) phosphorodichloridothiolate was reacted with 18 mL of anhydrous ammonia in 200 mL of methylene chloride to provide after workup 5.5 g (50.5%) of the desired S-(cyclohexyl) diamidophosphorothiolate (mp=115°–119° C.).

NMR(DMSOd$_6$): δ 4.32 (s, 4), 3.00 (m, 1), and 0.90–2.20 ppm (cp, 10);
IR(Nujol): 2.90–3.15 (bs), and 8.5μ.
HPLC analysis indicated a purity of 96%.

EXAMPLE VIII

Urease Inhibiting Efficacy Test

Representative compounds were tested to evaluate their efficacy in the inhibition of urease as compared to structurally similar compounds. The inhibition tests were run in a New York soil (Cazenovia silt loam, pH 7.2) and a Wisconsin soil (Plano silt loam, pH 5.4). Evaluations (run in triplicate) consisted of applying 800 micrograms of test compound in 5 mL of water and 42.8 mg of urea in 1 mL of water to 20 g of air dry soil in a glass bottle. The bottle was capped with perforated aluminum foil and incubated at 25° C. for 3 days prior to extraction with 100 mL of a 2M potassium chloride solution containing 0.5 mg of phenylmercuric acetate. The extracts were then analyzed for remaining urea using an autoanalyzer. Percent inhibition was calculated as % Inhibition = [1−(A−B/A−C)]×100% where A is urea recovered from unincubated sample (urea added to soil and immediately extracted); B is urea recovered from inhibited sample; and C is urea recovered from the control (uninhibited sample).

The results of these tests are set forth in the following Table I.

TABLE I

| | | Urease Efficacy Test | |
|---|---|---|---|
| Experiment | Compound | % Inhibition Cazenovia Soil | % Inhibition Wisconsin Soil |
| 1 | $CH_3SP(NH_2)_2$ with =O | 93 | 93 |
| 2* | $CH_3(CH_2)_3SP(NH_2)_2$ with =O | 74 | 82 |
| 3* | $CH_3CH_2CH(CH_3)SP(NH_2)_2$ with =O | 74 | 84 |
| 4* | $(CH_3)_2CHCH_2SP(NH_2)_2$ with =O | 80 | 83 |
| 5* | $CH_3(CH_2)_5-SP(NH_2)_2$ with =O | 52 | 66 |

TABLE I-continued

Urease Efficacy Test

| Experiment | Compound | % Inhibition Cazenovia Soil | % Inhibition Wisconsin Soil |
|---|---|---|---|
| 6* | 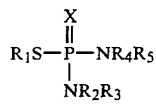 | 66 | 58 |
| Comp. Ex. 1 | $CH_3OP(NH_2)_2$ with $\mathrm{O}$ double bond | 34 | not determined |
| Comp. Ex. 2 | $CH_3CH_2CH_2OP(NH_2)_2$ with $\mathrm{O}$ double bond | 15 | not determined |

*These compounds were evaluated using only 200 micrograms instead of 800 micrograms of test compound per 20 g of soil.

What is claimed is:

1. A composition comprising a diluent or carrier and a urease inhibiting effective amount of one or more phosphorothiolate compounds of the formula $$R_1S-\underset{\underset{NR_2R_3}{|}}{\overset{\overset{X}{\|}}{P}}-NR_4R_5$$

wherein

X is oxygen or sulfur;

$R_1$ is substituted or unsubstituted alkyl, heterocycle, cycloalkyl, alkenyl, alkynyl, cycloalkenyl, aryl, aralkyl or alkaryl, wherein permissible substituents are one or more trihalomethyl, alkyl, halogen, phenoxy, phenyl, nitro, alkylmercapto, cyano, amino, isocyano, alkylamino, dialkylamino, isocyanato, alkoxy, mercapto, arylmercapto, alkylcarbonyl, arylamino, diarylamino, arylmercapto, arylcarbonyl, quaternary ammonium radicals, carboxy, carbonamide, hydroxy, heterocycle, alkoxy, aryloxy, cyano, or acyloxy; and $R_2$, $R_3$, $R_4$ and $R_5$ are individually hydrogen or alkyl having from 1 to 4 carbon atoms.

2. A composition according to claim 1 wherein said urease inhibiting effective amount is at least about 0.00001 weight percent based on the total weight of the composition.

3. A composition according to claim 2 wherein said amount is from about 0.00001 to about 98 weight percent.

4. A composition according to claim 3 wherein said amount is from about 0.002 to about 50 weight percent.

5. A composition according to claim 4 wherein said amount is from about 0.01 to about 20 weight percent.

6. A composition according to claim 5 wherein said amount is from about 0.1 to about 10 weight percent.

7. A composition according to claim 1 wherein X is oxygen.

8. A composition according to claim 1 wherein X is sulfur.

9. A composition according to claim 1 wherein $R_1$ is alkyl, or substituted alkyl having one or more substituents at the alpha, beta and/or gamma atoms relative to the sulfur atom to which the $R_1$ group is substituted, wherein permissible substituents are selected from the group consisting of iodo, chloro, phenyl, bromo, fluoro, phenoxy, p-nitrophenoxy, phenyl or phenyl substituted with 3-nitro, 4-nitro, 4-halo, 4-amino, 4-alkyl, 4-cyano, 4-alkoxy, 3-phenoxy, 3-pyridyl, 2-furyl, 2-naphthyl and cinnamenyl.

10. A composition according to claim 1 wherein $R_1$ is alkyl.

11. A composition according to claim 10 wherein $R_1$ is unsubstituted linear or branched chain alkyl having from 1 to about 12 carbon atoms.

12. A composition according to claim 11 wherein $R_1$ is alkyl having from about 1 to 8 carbon atoms.

13. A composition according to claim 12 wherein $R_1$ is alkyl having from 1 to about 8 carbon atoms.

14. A composition according to claim 13 wherein $R_1$ is alkyl having from 1 to about 6 carbon atoms.

15. A composition according to claim 1 wherein $R_1$ is unsubstituted cycloalkyl.

16. A composition according to claim 1 wherein $R_2$ $R_3$, $R_4$ and $R_5$ are hydrogen, methyl or ethyl.

17. A composition according to claim 16 wherein $R_2$, $R_3$, $R_4$ and $R_5$ are hydrogen.

18. A composition according to claim 1 wherein said one or more phosphorothiolate compounds are selected from the group consisting of S-methyl diamidophosphorothiolate, S-(n-butyl) diamidophosphorothiolate, S-(iso-butyl) diamidophosphorothiolate, S-(n-hexyl)-diamidophosphorothiolate and S-(cyclohexyl) diamidophosphorothiolate.

19. A composition according to claim 18 wherein said one or more phosphorothiolate compounds are selected from the group consisting of S-(n-butyl)-diamidophosphorothiolate S-(iso-butyl) diamidophosphorothiolate, S-(n-hexyl) diamidophosphorothiolate.

20. A composition according to claim 19 wherein said composition comprises a urease inhibiting effective amount of S-(n-butyl) diamidophosphorothiolate.

21. A composition according to claim 1 wherein

X is oxygen or sulfur;

$R_1$ is alkyl unsubstituted linear or branched chain alkyl having from 1 to about 10 carbon atoms; and $R_2$, $R_3$, $R_4$ and $R_5$ are hydrogen.

22. An improved fertilizer composition comprising urea or one or more urea precursor compounds capable of forming urea in situ when subjected to the use conditions of the composition and a urease inhibiting effective amount of one or more phosphorothiolate compounds of the formula:

$$R_1S-\underset{\underset{NR_4R_5}{|}}{\overset{\overset{X}{\|}}{P}}-NR_2R_3$$

wherein

X is oxygen or sulfur;

$R_1$ is substituted or unsubstituted alkyl, cycloalkyl, heterocycle, alkenyl, alkynyl, cycloalkyl, aralkyl, aryl or alkaryl, wherein permissible substituents are one more trihalomethyl, alkyl, isocyano, isocyanato, halogen, phenoxy, phenyl, nitro, cyano amino, alkylamino, arylamino, diarylamino, dialkylamino, alkoxy, arylmercapto, mercapto, alkylcarbonyl, arylcarbonyl, carboxy, heterocycle, alkylmercapto, carbonamide, hydroxy, alkoxy, aryloxy, cyano, or acyloxy; and $R_2$, $R_3$, $R_4$ and $R_5$ are individually hydrogen, or alkyl having from 1 to 4 carbon atoms.

23. A method of enhancing plant growth and/or crop yield of a plant growing in a plant growth media which comprises applying a plant growth and/or crop yield enhancing effective amount of the composition according to claim 22 to the plant growth media surrounding the plant.

24. A method of inhibiting the urease catalyzed hydrolysis of urea at a situs which comprises applying to said situs a urease inhibiting effective amount of one or more phosphorothiolate compounds of the formula:

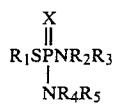

wherein:

X is oxygen or sulfur;

$R_1$ is substituted or unsubstituted alkyl, heterocycle, cycloalkyl, alkenyl, alkynyl, cycloalkenyl, aryl, aralkyl or alkaryl, wherein permissible substituents are one or more trihalomethyl, heterocycle, alkyl, halogen, phenoxy, mercapto, phenyl, nitro alkylmercapto, cyano, amino, alkylamino, dialkylamino, alkoxy, alkylcarbonyl, isocyano, isocyanato, arylamino, diarylamino, arylmercapto, arylcarbonyl, quaternary ammonium radicals, carboxy, carbonamide, hydroxy, alkoxy, aryloxy, cyano, or acyloxy; and $R_2$, $R_3$, $R_4$ and $R_5$ are individually hydrogen or alkyl having from 1 to 4 carbon atoms.

25. A method according to claim 24 wherein said situs is a plant growth media.

26. A method according to claim 25 wherein said one or more compounds are applied to said media prior to, subsequent to or in conjunction with the application of urea or one or more urea precursor compounds capable of forming urea in situ in the media.

27. A method according to claim 26 wherein said one or more phosphorothiolate compounds are applied to said media prior to application of urea and said urea precursor compounds thereto.

28. A method according to claim 24 wherein said urease inhibiting effective amount is at least about 0.1 ppm.

29. A method according to claim 28 wherein said amount is from about 0.01 to about 5,000 ppm.

30. A method according to claim 29 wherein said amount is from about 0.2 to about 100 ppm.

31. A method according to claim 30 wherein said amount is from about 1 to 500 ppm.

* * * * *

UNITED STATES PATENT AND TRADEMARK OFFICE
CERTIFICATE OF CORRECTION

PATENT NO. : 4,537,614

DATED : August 27, 1985

INVENTOR(S) : M. Van Der Puy et al.

It is certified that error appears in the above–identified patent and that said Letters Patent are hereby corrected as shown below:

Col. 20, line 22, "100 ppm" should read -- 1,000 ppm --.

Signed and Sealed this

Nineteenth Day of November 1985

[SEAL]

Attest:

DONALD J. QUIGG

Attesting Officer

Commissioner of Patents and Trademarks